United States Patent [19]

Alt et al.

[11] Patent Number: 5,045,554

[45] Date of Patent: Sep. 3, 1991

[54] SUBSTITUTED THIAZOLES AND THEIR USE AS FUNGICIDES

[75] Inventors: Gerhard H. Alt, University City; W. Gary Phillips, Glenco; John K. Pratt, St. Peters; Gabriel H. Srouji, Kirkwood, all of Mo.

[73] Assignee: Monsanto Company, St. Louis, Mo.

[21] Appl. No.: 414,667

[22] Filed: Oct. 3, 1989

Related U.S. Application Data

[63] Continuation-in-part of Ser. No. 277,375, Nov. 29, 1988, abandoned.

[51] Int. Cl.$^5$ .................. C07D 277/56; A01N 43/78
[52] U.S. Cl. ..................................... 514/365; 548/200
[58] Field of Search ..................... 548/194, 199, 200; 514/365

[56] References Cited

U.S. PATENT DOCUMENTS 3,547,917  12/1976  Kulka ................................. 548/194

FOREIGN PATENT DOCUMENTS 276177  7/1988  European Pat. Off. ........... 548/194
279239  8/1988  European Pat. Off. ........... 548/194
280275  8/1988  European Pat. Off. ........... 548/194

OTHER PUBLICATIONS

Eckstein, Chem Stosow, 25 19 (1981) C.A. 98:179261j.
Adbel-Lateff Acta Phytopathol. 8, 269, 1973 C.A. 81:115750j.

*Primary Examiner*—Robert Gerstl
*Attorney, Agent, or Firm*—Howard C. Stanley; Grace L. Bonner; Sta4ley M. Tarter

[57]  ABSTRACT

The present invention relates to certain substituted 5-carboxanilidothiazoles and their use as fungicides.

26 Claims, No Drawings

SUBSTITUTED THIAZOLES AND THEIR USE AS FUNGICIDES

RELATED APPLICATIONS

This application is a continuation-in-part of application Ser. No. 07/277,375 filed Nov. 29, 1988 now abandoned.

FIELD OF THE INVENTION

The present invention relates to certain substituted 5-carboxanilidothiazoles and their use as fungicides.

BACKGROUND OF THE INVENTION

Various substituted carboxanilidothiazoles are known in the art as fungicides. A known fungicide, 2-amino-4-methyl-5-(carboxyanilido)thiazole, is sold under the trademark Seedvax. European Patent Publication 0,276,177 discloses certain N-(indanyl) carboxamido thiazoles as fungicides including 2-methyl-4-trifluoromethyl-5-(N-[1,1,3 trimethylindan-4-yl]-carboxamido) thiazole. However, there still is a need in the art for fungicides which have the advantages of being safe on crops and efficacious at low application rates for cost savings and lower pesticide load on the environment.

SUMMARY OF THE INVENTION

The present invention relates to certain substituted 5-carboxanilidothiazoles and their use in the control of plant fungus diseases such as, for example Basidiomycetes. The carboxanilidothiazoles of the present invention are substituted on the thiazole ring as follows (the sulfur atom being the 1-position): in the 2-position on the thiazole ring —a $C_{1-2}$ haloalkyl or a lower alkyl substituent preferably $C_{1-2}$ alkyl and most preferably a methyl substituent; (ii) in the 4-position of the thiazole ring—a lower alkyl such as a $C_{1-2}$ alkyl or a $C_{1-2}$ haloalkyl, preferably halomethyl, more preferably perhalomethyl, most preferably trifluoromethyl, provided however the thiazole ring has at least one $C_{1-2}$ haloalkyl substituent, preferably a halomethyl substituent, in the 2-position or the 4-position and (iii) in the 5-position of the thiazole ring—a carboxanilido substituent uniquely having at least one electron withdrawing substituent on the phenyl ring preferably two to four electron withdrawing groups and most preferably, three to four electron withdrawing groups. The electron withdrawing groups are preferably selected from halo (preferably chloro, iodo or bromo), lower haloalkyl (preferably halo $C_{1-2}$ alkyl, more preferably perhalomethyl or trifluoromethyl) or lower haloalkoxy (preferably halo $C_{1-2}$ alkoxy, more preferably perhalomethoxy or trifluoromethoxy). Other suitable electron withdrawing ring substituents for compounds of the present invention include nitro, cyano, pentahalosulfur, preferably pentafluorosulfur, halomethylthio, haloethylthio, ($C_{1-2}$ alkyl or $C_{1-2}$ haloalkyl) sulfinyl or ($C_{1-2}$ alkyl or $C_{1-2}$ haloalkyl) sulfonyl. Haloethyl, haloethoxy, haloethylthio, haloethylsulfinyl and haloethylsulfonyl electron withdrawing substituents preferably have at least one halo substituent on the 1-carbon atom and most preferably two halo substituents on the 1-carbon atom. Preferably, electron withdrawing substituents are located in the ortho or para positions and most preferably in the ortho positions. Preferably the para substituent, if any, also has lipophilic character. Nitro and cyano substituents are not optimum as para substituents.

The open positions on the phenyl ring and the N atom of the carboxanilido group may also be substituted by a variety of other substituents other than hydrido which do not unacceptably interfere with the fungicidal activity of the molecule. Such substituents are preferably in the meta position and include lower alkyl, lower alkoxy, lower alkylthio, lower alkylcarbonyl, lower alkoxycarbonyl and the like. Other types of suitable substituents will be known to those skilled in the art.

The degree of substitution on the phenyl ring of the carboxanilido group will vary from 1 to 5 but unstable molecules such as those with trinitro substitution or tetra or penta iodo substitution are outside the scope of this invention. The compounds of the present invention have good fungicidal activity at low application rates, particularly on Basidiomycetes, and are generally safe to the environment including the host plant and animal life such as fish which the compounds may contact during use. A more thorough disclosure of the present invention is presented in detailed description which follows.

DETAILED DESCRIPTION

The present invention relates to certain substituted 5-carboxanilidothiazoles and their use in the control of plant fungus disease such as, for example Basidiomycetes such as Rhizoctonia, Sclerotium and Corticium.

A preferred embodiment of the unique class of 5-carboxanilidothiazoles of the present invention includes compounds represented by the Formula I and agronomically acceptable salts thereof:

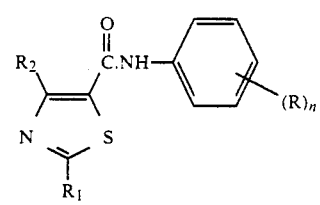

Formula I wherein each R is independently halo, halomethyl, 1-haloethyl, halomethoxy, 1-haloethoxy, halomethylthio, 1-haloethylthio, pentafluorosulfur, halomethylsulfinyl, 1-haloethylsulfinyl, halomethylsulfonyl or 1-haloethylsulfonyl; $R_1$ and $R_2$ are independently methyl, ethyl, or halomethyl provided at least one of $R_1$ or $R_2$ is halomethyl, and n is from 1 to 5. Preferably, R is selected from chloro, bromo, iodo, trihalomethyl, (most preferably trifluoromethyl) or trihalomethoxy (most preferably trifluoromethoxy). Preferably n is 2-5, more preferably n is 3-5 and most preferably n is 3-4. The R substituents are preferably in the ortho and/or para positions and preferably both ortho positions have an R substituent. In one preferred class of compounds, $R_1$ is methyl and $R_2$ is perhalomethyl and most preferably trifluoromethyl. In another preferred class of compounds, $R_1$ and $R_2$ are each perhalomethyl and most preferably trifluoromethyl. In another preferred class $R_1$ is difluoromethyl and $R_2$ is trifluoromethyl.

The term "carboxanilido" means $C_6H_5NHCO-$. The term "1-haloethyl" means $CX_cH_{3-c}-CXH_{2-d}$ —where X is halo, c is 0-3 and d is 1 or 2. The term "1-haloethoxy" means 1-haloethyl-O-. The term "1-haloethylsulfonyl" means 1-haloethyl-$SO_2-$. The term "lower alkyl" means $C_{1-5}$ alkyl.

Open positions on the phenyl ring of Formula I which do not have an R substituent may be substituted by other substituents which either enhance the activity of the molecule or do not unacceptably hinder the activity. Molecules having such substituents are contemplated as equivalents of the compounds claimed herein. Such substituents may include nitro, cyano, alkylthio, $C_{1-2}$ alkylsulfinyl, $C_{1-2}$ alkylsulfonyl, lower alkyl, lower alkoxy, lower alkylcarbonyl or lower alkoxycarbonyl.

Those skilled in the art will be able to select other types of suitable substituents.

Another preferred embodiment of the unique class of 5-carboxanilidothiazoles of the present invention includes compounds represented by the Formula II and agronomically acceptable salts thereof:

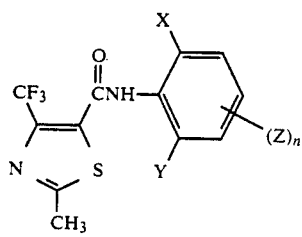

Formula II wherein X is halo, trihalomethyl or trihalomethoxy; Y is halo, trihalomethyl, trihalomethoxy, nitro or cyano; each Z is independently halo, trihalomethyl, trihalomethoxy, nitro or cyano; and n is 0 to 3.

Preferably X, Y and Z are independently halo, trifluoromethyl or trifluoromethoxy, especially for a para Z substituent. Preferred halogens for X, Y and Z are chloro, bromo or iodo and n is preferably or 2.

Open positions on the phenyl ring of Formula II which do not have a Z substituent may be substituted by other substituents which either enhance the activity of the molecule or do not unacceptably hinder the activity such as electronegative substituents as described herein or substituents such as lower alkyl, lower alkoxy, lower alkylthio, lower alkylcarbonyl, or lower alkoxycarbonyl. Compounds having such substituents are contemplated as equivalents of the compounds claimed herein.

Another preferred embodiment of the unique class of 5-carboxanilidothiazoles of the present invention includes compounds represented by the Formula III and agronomically acceptable salts thereof:

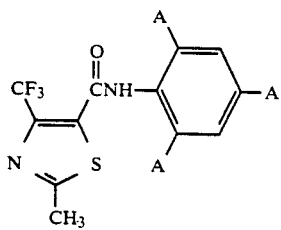

Formula III wherein each A is independently selected from halo, trifluoromethyl or trifluoromethoxy. A as halo is preferably chloro, bromo or iodo.

Open positions on the phenyl ring of Formula III may be substituted by other substituents which either enhance the activity of the molecule or do not unacceptably hinder the activity such as electronegative substituents as described herein or substituents such as lower alkyl, lower alkoxy, lower alkylthio, lower alkylcarbonyl or lower alkoxycarbonyl. Compounds having such substituents are contemplated as equivalents of the compounds claimed herein.

Another preferred embodiment of the unique class of 5-carboxanilidothiazoles of the present invention includes compounds represented by the Formula IV and agronomically acceptable salts thereof:

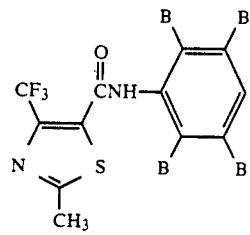

Formula IV wherein each B is independently halo, trifluoromethyl or trifluoromethoxy. B as halo is preferably chloro, or bromo.

The open position on the phenyl ring of Formula IV may be substituted by other substituents which either enhance the activity of the molecule or do not unacceptably hinder the activity such as electronegative substituents as described herein or a substituents such as lower alkyl, lower alkoxy, lower alkylthio, lower alkylcarbonyl or lower alkoxycarbonyl. Compounds having such substituents are contemplated as equivalents of the compounds claimed herein.

Agronomically acceptable salts of the present invention include alkali, alkaline earth, acid addition, base addition and alkylation salts.

The procedures described below depict suitable methods whereby the compounds of this invention may be prepared by known chemical procedures from compounds which are known in the art and/or are readily available commercially. These procedures described below are merely illustrative and those skilled in the art will know a variety of other procedures suitable for use in making the compounds of the present invention.

Compounds of the present invention can be prepared by reacting an appropriately substituted thiazole having a 5-carbonylchloride substituent with an appropriately substituted aniline in suitable solvent(s) at an elevated temperature. Suitable solvents include xylene, THF, toluene, chlorobenzene, collidine, and 2,6-di-t-butyl-4-methyl pyridine. In some cases, acid acceptors such as tertiary amines and pyridines may be used to accelerate the rate of reaction.

Appropriately substituted anilines are commercially available or may be prepared by standard chemical procedures. For example, halo substituted anilines can be prepared by halogenation of anilines using standard techniques.

The thiazoles are conveniently prepared by reacting ethyl 4,4,4 trifluoro-2-chloroacetoacetate with thioacetamide in a suitable solvent, preferably DMF to form ethyl 2-methyl-4-trifluoromethyl-5-thiazolecarboxylate which can be converted into the corresponding acid chloride with sequential hydrolysis with base and reaction with thionyl chloride.

The 2-haloalkyl thiazoles are conveniently prepared by the following sequential reactions: (i) reacting a readily available amide with, for example, Lawesson's reagent to yield the corresponding thioamide. The thioamide can be unstable and it is generally best to store it cold and to utilize it within a few days; (ii) reacting the thioamide with ethyl 4,4,4 trifluoromethyl-2- chloroacetoacetate in a suitable solvent, such as DMF or THF in the presence of a base such as sodium bicarbonate or potassium carbonate to form the ethyl 2-haloalkyl-4-trifluoromethyl-5-thiazole-carboxylate; and (iii) converting the above product to the acid chloride by a saponification with sodium hydroxide followed by reaction with oxalyl chloride.

The following Examples 1-2 are detailed descriptions of methods of preparation of certain compounds of the present invention. These detailed preparations fall within the scope of, and serve to exemplify, the more generally described methods of preparation set forth above. These Examples are presented for illustrative purposes only and are not intended as a restriction on the scope of the invention.

EXAMPLE 1

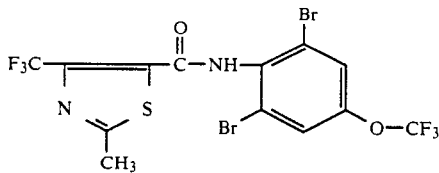

2=methyl-4-trifluoromethyl-5-(2',6,-dibromo-4'-trifluoromethoxy carboxanilido) thiazole (a) 21.8g (0.1 mole) of ethyl 4,4,4, trifluoro-2-chloro-acetoacetate was combined with 7.5 g (0.1 mole) of thioacetamide in 200 ml of DMF and refluxed overnight. The mixture was then mixed with water and extracted with ether. The ether extracts were washed with water and brine, dried over magnesium sulfate, filtered through silica gel, rotovapped and distilled (Kugelrohr) to provide 9.0 g (38%) of a yellow-brown solid, 2-methyl-4-trifluoromethyl-5-ethoxycarbonyl thiazole.

(b) 9.0 g (0.038 mole) of the ester of step (a) was stirred overnight with 1.6 g (0.04 mole) of sodium hydroxide in 50 ml of water. This mixture was cooled with ice water and 10% HCl was added dropwise until pH of 1. This mixture was extracted with ether. The ether was washed with water and brine, dried over magnesium sulfate and rotovapped to give 7.5 g (93.5%) of a white solid 2-methyl-4-trifluoromethyl-5-thiazole carboxylic acid.

(c) 7.5 g (0.0355 mole) of the product of step (b) was combined and heated overnight with 30 ml of thionyl chloride. The mixture was cooled, rotovapped to remove excess thionyl chloride and distilled (Kugelrohr) to give 5 g (61%) of a yellow oil, 2-methyl-4-trifluoromethyl-5-chlorocarbonyl thiazole b.p. 50°-52° C. at (0.05 torr).

(d) 8.85 g (0.05 mole) of 4-trifluoromethoxy aniline was combined with 8.4 g of (0.10 mole) of sodium acetate, 90 ml of glacial acetic acid and 16 g (0.10 mole) of bromine and heated at 60° C. for 2 hours.

The mixture was stirred at room temperature overnight. Water was added to the mixture and the mixture was filtered to give 16.0 g of an off-white crystalline solid m.p. 65°-67° C., 2,6 dibromo-4-trifluoromethoxy aniline.

(e) 2.07 g (0.009 mole) of the product of step c was combined with 2.68 g (0.008 mole) of the product of step (d) in 100 ml of xylenes and refluxed for 24 hours. The mixture was then extracted sequentially with 10% HCl and water, dried over magnesium sulfate and concentrated under a vacuum to give a solid. The solid was recrystallized from ethyl acetate/cyclohexane to give a 2.54 g (53%) of a white solid m.p. 172°-173° C.

Elemental Analysis for $C_{13}H_6N_2O_2S\ F_6BR_2$

| Elemental Analysis for $C_{13}H_6N_2O_2S\ F_6Br_2$ | | | |
|---|---|---|---|
| | C | H | N |
| Calculated | 29.57 | 1.15 | 5.30 |
| Found | 29.50 | 1.15 | 5.26 |

EXAMPLE 2

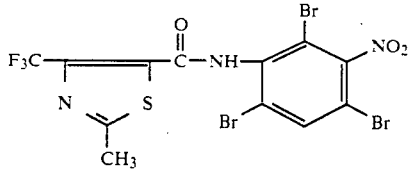

2-Methyl-4-dtrifuloromethyl-5-(2',4',6'-tribromo-3'-nitrocarboxanilido) thiazole.

(a) 6.9 g (0.05 mole) of m-nitroaniline, 12.6 g (0.15 mole) of sodium acetate, 24.0 g (0.15 mole) of bromine in 120 ml of glâcial acetic acid were heated to reflux for 6 hours. The mixture was then added to water and filtered to give 15.1 g of a pale yellow solid 2,4,6 tribromo-3-nitroaniline m.p. 101°-103° C.

(b) 3.75 g (0.008 mole) of the product of step a was combined with 2.3 g (0.01 mole) of 2-methyl-4-trifluoromethyl-5-chlorocarbonyl thiazole and 2.05 g (0.01 mole) of 2,6 di-t-butyl-4-methyl pyridine and heated with stirring for 2 hours. The mixture was then dissolved in ethyl acetate, extracted with 10% HCl and water, dried over MgSO₄ and rotovapped to remove the ethyl acetate. The solid was recrystallized from ethyl acetate/hexanes to give 3.5 g (77%) of a tan solid m.p. 244°-246° C.

Elemental Analysis for $C_{12}H_5N_3O_3SF_3Br_3$

| Elemental Analysis for $C_{12}H_5N_3O_3SF_3Br_3$ | | | |
|---|---|---|---|
| | C | H | N |
| Calculated | 25.38 | 0.89 | 7.40 |
| Found | 25.46 | 0.92 | 7.37 |

Using procedures similar to those set out in detail above, further compounds of the present invention were prepared and are shown in the following Table I.

| Ex | CP # | Name | Structure |
|---|---|---|---|
| | 3 | 5-thiazolecarboxamide, 2-methyl-N-(pentafluorophenyl)-4-(trifluoromethyl)-<br>MP: 111.0–112.0 nD: | |
| | 4 | 5-thiazolecarboxamide, 2-methyl-N-(2,4,6-trichlorophenyl)-4-(trifluoromethyl)-<br>MP: 167.0–169.0 nD: | |
| | 5 | 5-thiazolecarboxamide, N-(2,4-dibromo-6-nitrophenyl)-2-methyl-4-(trifluoromethyl)-<br>MP: 203.0–204.0 nD: | |
| | 6 | 5-thiazolecarboxamide, N-(2,4-dichloro-6-nitrophenyl)-2-methyl-4-(trifluoromethyl)-<br>MP: 167.0–169.0 nD: | |
| | 7 | 5-thiazolecarboxamide, N-(2-bromo-4-chloro-6-nitrophenyl)-2-methyl-4-(trifluoromethyl)-<br>MP: 180.0–181.0 nD: | |
| | 8 | 5-thiazolecarboxamide, 2-methyl-N-(pentachlorophenyl)-4-(trifluoromethyl)-<br>MP: 229.0–231.0 nD: | |
| | 9 | 5-thiazolecarboxamide, N-[2,6-dibromo-4-chloro-3-(trifluoromethyl)phenyl]-2-methyl-4-(trifluoromethyl)-<br>MP: 188.0–190.0 nD: | |
| | 10 | 5-thiazolecarboxamide, 2-methyl-N-(2,4,6-tribromo-3-cyanophenyl)-4-(trifluoromethyl)-<br>MP: 232.0–234.0 nD: | |
| | 11 | 5-thiazolecarboxamide, N-[2,6-dibromo-4-(trifluoromethyl)phenyl]-2-methyl-4-(trifluoromethyl)-<br>MP: 190.0–193.0 nD: | |

-continued

| Ex CP # | Name | Structure |
|---|---|---|
| 12 | 5-thiazolecarboxamide, N-(4,6-dibromo-2-cyano-3-fluorophenyl)-2-methyl-4-(trifluoromethyl)-<br>MP: 183.0–185.0 nD: | 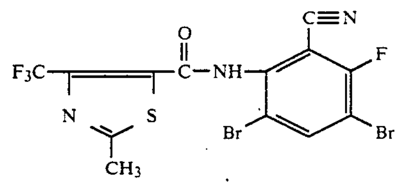 |
| 13 | 5-thiazolecarboxamide, N-[2-chloro-4-(trifluoromethyl)-6-nitrophenyl]-2-methyl-4-(trifluoromethyl)-<br>MP: 179.0–181.0 nD: | 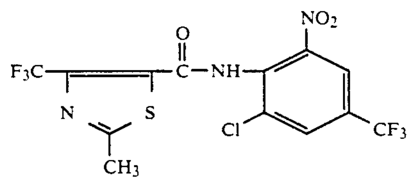 |
| 14 | 5-thiazolecarboxamide, 2-methyl-N-(2,4,6-tribromophenyl)-4-(trifluoromethyl)-<br>MP: 208.0–210.0 nD: | 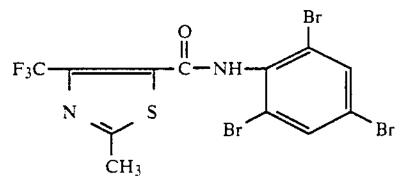 |
| 15 | 5-thiazolecarboxamide, N-(2,6-dichloro-4-iodophenyl)-2-methyl-4-(trifluoromethyl)-<br>MP: 197.0–199.0 nD: | 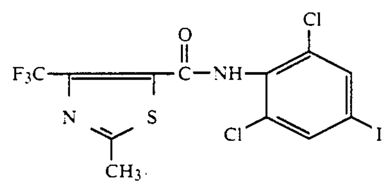 |
| 16 | 5-thiazolecarboxamide, N-(2,4-dibromo-6-cyanophenyl)-2-methyl-4-(trifluoromethyl)-<br>MP: 182.0–184.0 nD: | 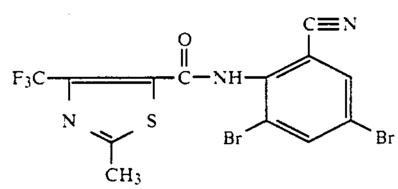 |
| 17 | 5-thiazolecarboxamide, N-[2-bromo-6-nitro-4-(trifluoromethyl)phenyl]-2-methyl-4-(trifluoromethyl)-<br>MP: 196.0–197.0 nD: | 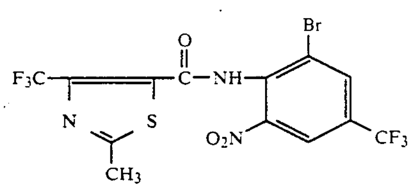 |
| 18 | 5-thiazolecarboxamide, N-[2,4-dibromo-6-(trifluoromethyl)phenyl]-2-methyl-4-(trifluoromethyl)-<br>MP: 202.0–204.0 nD: | 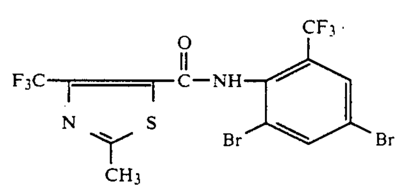 |
| 19 | 5-thiazolecarboxamide, 2-methyl-N-(2,3,5,6-tetrachlorophenyl)-4-(trifluoromethyl)-<br>MP: 232.0–234.0 nD: | 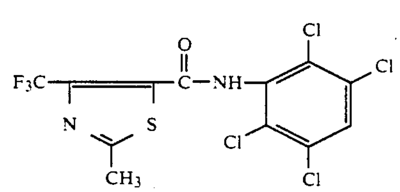 |

-continued

| Ex CP # | Name | Structure |
|---|---|---|
| 20 | 5-thiazolecarboxamide, N-(2,6-bromo-4-iodophenyl)-2-methyl-4-(trifluoromethyl)-<br>MP: 221.0–223.0 nD: | 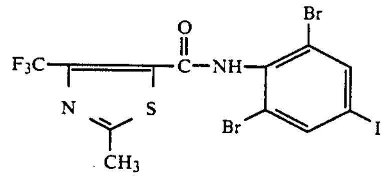 |
| 21 | 5-thiazolecarboxamide, N-(2,4-dibromo-3,6-dicyanophenyl)-2-methyl-4-(trifluoromethyl)-<br>MP: 211.0–213.0 nD: | 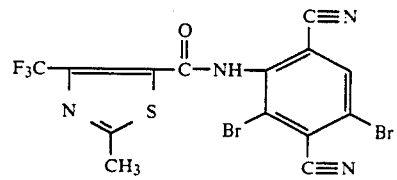 |
| 22 | 5-thiazolecarboxamide, N-[2,6-dichloro-4-(trifluoromethyl)phenyl]-2-methyl-4-(trifluoromethyl)-<br>MP: 162.0–163.0 nD: | 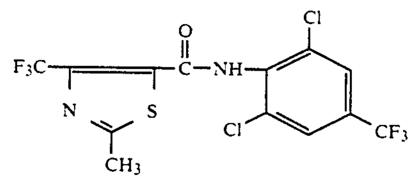 |
| 23 | 5-thiazolecarboxamide, N-(2-acetyl-4,6-dibromophenyl)-2-methyl-4-(trifluoromethyl)-<br>MP: 164.0–166.0 nD: | 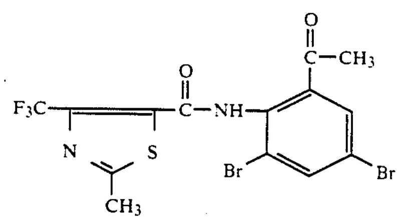 |
| 24 | 5-thiazolecarboxamide, N-[2,6-dichloro-4-(trifluoromethoxy)phenyl]-2-methyl-4-(trifluoromethyl)-<br>MP: 151.0–152.0 nD: | 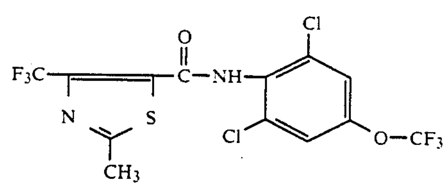 |
| 25 | 5-thiazolecarboxamide, 2-ethyl-N-(2,4,6-trichlorophenyl)-4-(trifluoromethyl)-<br>MP: 127.0–130.0 nD: | 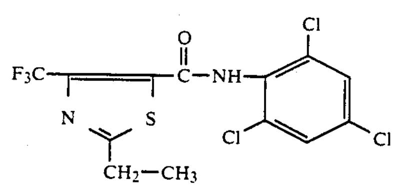 |
| 26 | 5-thiazolecarboxamide, N-(4-bromo-2,6-dicyanophenyl)-2-methyl-4-(trifluoromethyl)-<br>MP: 217.0–219.0 nD: | 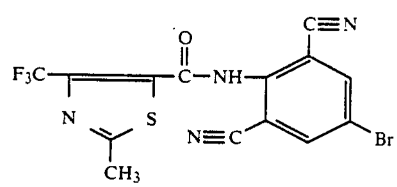 |
| 27 | 5-thiazolecarboxamide, 4-(difluoromethyl)-2-methyl-N-(2,4,6-tribromophenyl)-<br>MP: 163.0–165.0 nD: | 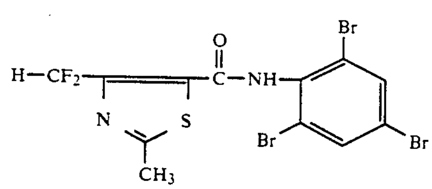 |

| Ex CP # | Name | Structure |
|---|---|---|
| 28 | 5-thiazolecarboxamide, N-[2,6-dibromo-4-(trifluoromethoxy)phenyl]-4-(difluoromethyl)-2-methyl- MP: 160.0–162.0 nD: | 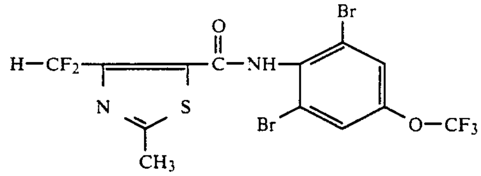 |
| 29 | sulfur, [3,5-dibromo-4-[[[2-methyl-4-(trifluoromethyl)-5-thiazolyl]carbonyl]amino]phenyl]pentafluoro- MP: 174.0–176.0 nD: | 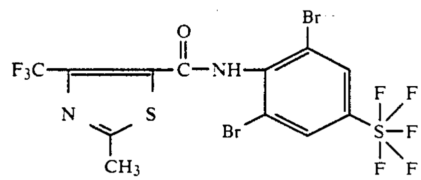 |
| 30 | 5-thiazolecarboxamide, N-(2,4,6-trichlorophenyl)-2,4-bis(trifluoromethyl)- MP: 180.0–181.0 nD: | 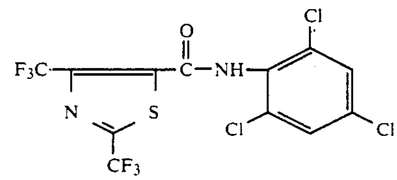 |
| 31 | 5-thiazolecarboxamide, N-(pentachlorophenyl)-2,4-bis(trifluoromethyl)- MP: 230.0–231.0 nD: | 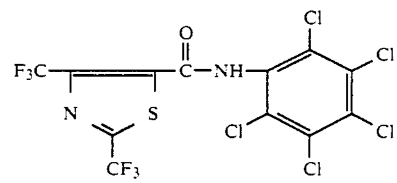 |
| 32 | 5-thiazolecarboxamide, N-(2,4,6-tribromphenyl)-2,4-bis(trifluoromethyl) MP: 204.0–205.0 nD: | 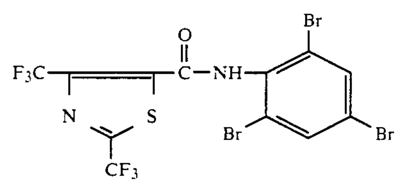 |
| 33 | 5-thiazolecarboxamide, N-(pentafluorophenyl)-2,4-bis(trifluoromethyl)- MP: 143.0–145.0 nD: | 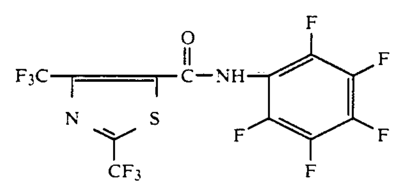 |
| 34 | 5-thiazolecarboxamide, N-[2,6-dibromo-4-(trifluoromethoxy)phenyl]-2,4-bis(trifluoromethyl)- MP: 167.0–168.5 nD: | 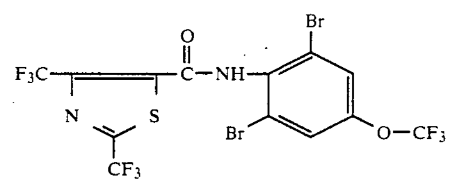 |
| 35 | 5-thiazolecarboxamide, 2-(difluoromethyl)-N-(2,4,-6-tribromophenyl)-4-(trifluoromethyl)- MP: 215.0–217.0 nD: | 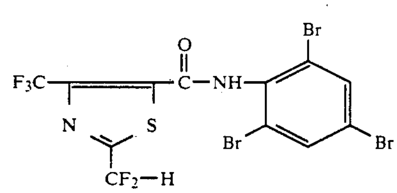 |
| 36 | 5-thiazolecarboxamide, N-[2,6-dibromo-4-(trifluoromethoxy)phenyl]-2-(difluoromethyl)-4-(trifluoromethyl)- MP: 196.0–198.0 nD: | 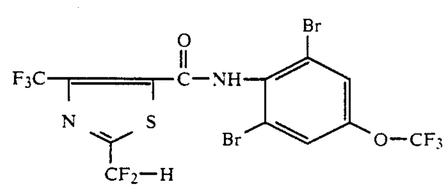 |

| Ex CP # | Name | Structure |
|---|---|---|
| 37 | 5-thiazolecarboxamide, 4-methyl-N-(2,4,6-tribromophenyl)-2-(trifluoromethyl)- MP: 200.0-201.0 nD: | (structure: 4-methyl-2-(trifluoromethyl)thiazole-5-carboxamide with 2,4,6-tribromophenyl) |
| 38 | 5-thiazolecarboxamide, N-[2,6-dibromo-4-(trifluoromethoxy)phenyl]-4-methyl-2-(trifluoromethyl)- MP: 162.0-169.0 nD: | (structure: 4-methyl-2-(trifluoromethyl)thiazole-5-carboxamide with 2,6-dibromo-4-(trifluoromethoxy)phenyl) |
| 39 | 5-thiazolecarboxamide, 2-(difluoromethyl)-4-methyl-N-(2,4,6-tribromophenyl)- MP: 188.0-189.0 nD: | (structure: 2-(difluoromethyl)-4-methylthiazole-5-carboxamide with 2,4,6-tribromophenyl) |
| 40 | 5-thiazolecarboxamide, N-[2,6-dibromo-4-(trifluoromethoxy)phenyl]-2-(difluoromethyl)-4-methyl- MP: 150.0-151.0 nD: | (structure: 2-(difluoromethyl)-4-methylthiazole-5-carboxamide with 2,6-dibromo-4-(trifluoromethoxy)phenyl) |

PRIMARY TEST FOR ACTIVITY ON RICE SHEATH BLIGHT

The *Rhizoctonia solani* is cultured on rice grain inoculum at room temperature in darkness in the laboratory. Inoculum is prepared by mixing one part rice grain, one part chopped rice grain and one part water. The mixture is autoclaved twice before use. Sclerotia are added to each flask and the inoculum is ready for use when mycelia of *Rhizoctonia solani* have ramified throughout the medium and new sclerotia have formed (generally in about four to eight weeks).

Rice plant seeds, 16–18, are planted in the center of a 7.62 cm square pot and covered with steam sterilized soil (silt loan, rediearth and osmocote). The pots are placed in greenhouse at 25°–30° C. and with 14 hours of lighting. In about 11–15 days the plants are in the second to third leaf stage and ready for testing.

The test compounds are diluted to 1% by weight solution in acetone. Prior to application, the test solutions are prepared in concentrations of 0.5; 0.1 and 0.02 mg/ml having a formulation of 40% acetone, 0.4% Tween-20 and 59.6% water.

Plants are sprayed at the second to third leaf stage. Two ml of the formulation is drenched onto the soil of the pot, approximately 1.5 ml/pot is then foliarly applied using a "Devilbiss 152" atomizer. The atomizer is rinsed with acetone between treatments.

The rice plants are allowed to air dry at room temperature before being returned to the greenhouse. The pots are placed into a specially fabricated plastic flood tray. There are no drain holes in the trays so water is retained in the system.

All pots are kept in the flood trays, which are filled with water to the soil line before inoculation. Two days later, approximately 2 grams of the inoculum is applied to each pot at the base of the clump of rice. The trays are then placed into a dark growth room at 100% relative humidity and 25 C. After at least 24 hours of darkness, the lights are turned onto a 12 hour light cycle. The plants are left undisturbed for 4 to 7 days and then rated for disease control. Disease control is assessed on the presence and severity of Sheath Blight lesions as compared to control pots. One rating for each treatment (four pots) is taken.

The following rating scale is used:
0 = No activity
1 = Low activity
2 = Moderate activity
3 = High activity Table II summarizes the results of tests conducted to determine the fungicidal activity of the compounds of this invention.

TABLE II

| Example | Concentration of Test Soln (mg/ml) | Activity Rating |
|---|---|---|
| 1 | 0.5/0.1/0.02 | 3/3/2 |
| 2. | 0.5/0.1/0.02 | 3/2/2 |
| 4 | 0.5/0.1/0.02 | 3/2/1* |
| 8 | 0.5/0.1/0.02 | 3/3/3 |
| 10 | 0.5/0.1/0.02 | 3/3/3 |
| 11 | 0.5/0.1/0.02 | 3/3/0 |
| 14 | 0.5/0.1/0.02 | 2.66*/3/3 |
| 15 | 0.5/0.1/0.02 | 1.66*/1*/0 |
| 16 | 0.5/0.1/0.02 | 3/2/3 |
| 17 | 0.5/0.1/0.02 | 1.5*/1/0 |
| 19 | 0.5/0.1/0.02 | 3/3/3 |
| 20 | 0.5/0.1/0.02 | 3*/3*/1.5* |
| 21 | 0.5/0.1/0.02 | 0/1/0 |
| 22 | 0.1/0.02 | 3/3 |
| 23 | 0.5/0.1/0.02 | 3/3/3 |

TABLE II-continued

| Example | Concentration of Test Soln (mg/ml) | Activity Rating |
|---|---|---|
| 24 | 0.5/0.1/0.02 | 3/3/2 |
| 27 | 0.5/0.1/0.02 | 3/1/0 |
| 28 | 0.5/0.1/0.02 | 3/2/0 |
| 29 | 0.5/0.1/0.02 | 3/0/0 |
| 30 | 0.5/0.1/0.02 | 3/3/0 |
| 31 | 0.5/0.1/0.02 | 1/1/1 |
| 32 | 0.5/0.1/0.02 | 3/3/1 |
| 33 | 0.5/0.1/0.02 | + |
| 34 | 0.5/0.1/0.02 | 3/3/1 |
| 35 | 0.5/0.1/0.02 | 2/2/2 |
| 36 | 0.5/0.1/0.02 | 3/3/3 |
| 37 | 0.5/0.1/0.02 | 3/3/3 |
| 38 | 0.5/0.1/0.02 | 3/2/2 |
| 39 | 0.5/0.1/0.02 | 3/2/2 |
| 40 | 0.5/0.1/0.02 | 3/3/2 |

*average of 2 or more test replications
+ phytotoxicity

ADVANCE TESTING FOR ACTIVITY ON RICE SHEATH BLIGHT

The host seeds are planted and *R. solani* is cultured as previously described. The plants are inoculated at the three leaf stage. To inoculate the plants, the inoculum is removed from the flasks, broken into small bits or individual grains and a small amount (1 cm$^3$) is added to the base of each clump of rice plants. After inoculation, the plants are moved to a dark growth room set for fog and 25C. Lights are returned to a 12 hour day/night cycle after 24 hours of darkness.

The test solutions are prepared in the same manner as in the primary test.

For foliar application, the plants are sprayed when the third leaf is fully expanded but the fourth leaf has not emerged. The surface of all pots is covered with a layer of vermiculite before chemical application which is removed immediately after application for all foliar spray tests. Compounds are applied using a DeVilbiss air-brush sprayer. Two ml/pot volume is applied which is enough to cover all surfaces of the plants to wetness but not enough to cause the material to drip from the leaves. Plants are moved to the drying room after spraying (very low light conditions) and after 3-4 hours are moved to the greenhouse bench. If plants are planted on day "0", then typically the chemical is applied on day 14, and pathogen inoculation occurs on day 16. Evaluation of disease will be made on day 26 to 30. Disease is evaluated by estimating the amount of stem tissue that is covered by symptoms; water soaking, chlorosis and necrosis and converted to a percent control as compared to the formulation treated check.

The protocol for the soil drench protective test is identical to that of the foliar protectant test except for the method of applying the chemical. Chemical test solutions are prepared and are applied to the soil surface with a pipette (1 ml/pot). Plants are moved to the greenhouse within 30 minutes of treatment. Plants are watered immediately with sufficient water to fill the top of the pot and kept for 2 days with the soil saturated. Inoculation, incubation and evaluation are made on the same schedule and in the same manner as the foliar protectant test.

Table III summarizes the results of tests conducted to determine the fungicidal activity of the compounds of this invention.

TABLE III

| Example | Test | Concentration of Test Solution* | % of Control |
|---|---|---|---|
| 1 | Foliar | 0.1 | 98 |
|  |  | 0.05 | 100 |
|  |  | 0.02 | 59+ |
|  |  | 0.01 | 32+ |
|  | Soil | 1.00 | 67 |
|  |  | 0.20 | 37 |
| 2 | Foliar | 0.1 | 87 |
|  |  | 0.05 | 97 |
|  |  | 0.02 | 84 |
|  |  | 0.01 | 64 |
|  | Soil | 1.00 | 47 |
|  |  | 0.20 | 8 |
| 3 | Foliar | 0.1 | 15 |
|  |  | 0.02 | 3 |
| 4 | Foliar | 0.05 | 29+ |
|  |  | 0.02 | 17 |
|  |  | 0.01 | 15 |
| 5 | Foliar | 0.1 | 58 |
|  |  | 0.02 | 6 |
| 6 | Foliar | 0.1 | 15 |
|  |  | 0.02 | 15 |
| 7 | Foliar | 0.5 | 94 |
|  |  | 0.1 | 72 |
|  |  | 0.02 | 27 |
|  | Soil | 1.00 | 85 |
|  |  | 0.20 | 10 |
|  |  | 0.04 | 23 |
| 8 | Foliar | 0.5 | 100 |
|  |  | 0.1 | 100 |
|  |  | 0.05 | 98 |
|  |  | 0.02 | 97+ |
|  |  | 0.01 | 86 |
|  |  | 0.002 | 71 |
| 8 | Soil | 1.00 | 39 |
|  |  | 0.20 | 65 |
|  |  | 0.04 | -1 |
| 9 | Foliar | 0.02 | 99 |
|  |  | 0.01 | 93 |
|  |  | 0.002 | 95 |
|  | Soil | 0.04 | 41 |
|  |  | 0.02 | 11 |
| 10 | Foliar | 0.1 | 93 |
|  |  | 0.05 | 98 |
|  |  | 0.02 | 85 |
|  |  | 0.01 | 45 |
|  | Soil | 1.00 | 38 |
|  |  | 0.20 | 18 |
| 11 | Foliar | 0.5 | 99 |
|  |  | 0.1 | 90 |
|  |  | 0.02 | 43 |
|  | Soil | 1.00 | 71 |
|  |  | 0.20 | 57 |
|  |  | 0.04 | 8 |
| 12 | Foliar | 0.1 | 42 |
|  |  | 0.02 | 30 |
| 13 | Foliar | 0.02 | 21 |
|  |  | 0.01 | 6 |
| 14 | Foliar | 0.5 | 91 |
|  |  | 0.1 | 93 |
|  |  | 0.05 | 70 |
|  |  | 0.02 | 10 |
|  |  | 0.01 | 20 |
| 16 | Foliar | 0.1 | 84 |
|  |  | 0.02 | 24 |
|  |  | 1.00 | 58 |
|  |  | 0.20 | 20 |
| 17 | Foliar | 0.1 | 81 |
|  |  | 0.02 | 38 |
| 18 | Foliar | 0.02 | 71 |
|  |  | 0.01 | 30 |
| 19 | Foliar | 0.5 | 100 |
|  |  | 0.01 | 72 |
|  |  | 0.02 | 96 |
|  |  | 0.005 | 44 |
|  | Soil | 1.00 | 18 |
|  |  | 0.20 | 11 |
|  |  | 0.04 | -3 |
| 20 | Foliar | 0.5 | 100 |
|  |  | 0.1 | 97 |
|  |  | 0.02 | 41 |

TABLE III-continued

| Example | Test | Concentration of Test Solution* | % of Control |
|---|---|---|---|
| | | 0.005 | 13 |
| | Soil | 1.00 | 36 |
| | | 0.20 | 12 |
| | | 0.04 | 13 |
| 24 | Foliar | 0.5 | 100 |
| | | 0.1 | 97 |
| | | 0.02 | 59 |
| | Soil | 1.00 | 91 |
| | | 0.20 | 52 |
| | | 0.04 | 26 |
| 25 | Foliar | 1.0 | 87 |
| | | 0.5 | 32 |
| | | 0.1 | 8 |
| | Soil | 2.0 | 23 |
| | | 1.0 | 12 |
| 26 | Foliar | 0.5 | 72 |
| | | 0.1 | 66 |
| | | 0.02 | 40 |
| | Soil | 2.0 | 0 |
| | | 1.0 | 60 |
| 30 | Foliar | 0.5 | 98 |
| | | 0.1 | 64 |
| | | 0.02 | 20 |
| | Soil | 1.00 | 75 |
| | | 0.20 | 73 |
| | | 0.04 | 27 |
| 31 | Foliar | 0.5 | 83 |
| | | 0.1 | 87 |
| | | 0.02 | 63 |
| | Soil | 1.00 | 40 |
| | | 0.20 | 47 |
| | | 0.04 | 28 |
| 32 | Foliar | 0.5 | 99 |
| | | 0.1 | 100 |
| | | 0.02 | 79 |
| | Soil | 1.00 | 49 |
| | | 0.20 | 20 |
| | | 0.04 | 28 |
| 34 | Foliar | 0.5 | 99 |
| | | 0.1 | 96 |
| | | 0.02 | 54 |
| | Soil | 1.00 | 67 |
| | | 0.20 | 69 |
| | | 0.04 | 14 |
| 36 | Foliar | 0.1 | 100 |
| | | 0.02 | 97 |
| | Soil | 1.00 | 84 |
| | | 0.20 | 71 |
| 37 | Foliar | 0.5 | 100 |
| | | 0.1 | 96+ |
| | | 0.02 | 68+ |
| | Soil | 1.00 | 25+ |
| | | 0.20 | 16+ |
| | | 0.04 | 12 |
| 38 | Foliar | 0.1 | 85 |
| | | 0.02 | 25 |
| | Soil | 1.00 | 48 |
| | | 0.20 | −4 |
| 39 | Foliar | 0.1 | 87 |
| | | 0.02 | 30 |
| | Soil | 1.00 | 21 |
| | | 0.20 | 21 |
| 40 | Foliar | 0.1 | 95 |
| | | 0.02 | 21 |
| | Soil | 1.00 | 70 |
| | | 0.20 | 21 |

*Foliar is mg/ml - soil drench is mg/pot
+ Average of 2 or more tests

TEST FOR ACTIVITY ON BROWN PATCH

Creeping bentgrass was grown in greenhouse in 12.7 cm diameter plastic pots for a period of 6 weeks. One day prior to test initiation the turf was mowed to approximately one inch in height. The test compounds were formulated as flowables. The formulated materials were dissolved in appropriate amount of water to give final test solutions having concentrations of 1, 0.2 and 0.04 mg/ml of active ingredient.

Four pots or replicates were used for each treatment with each test pot receiving 5 ml of test solution. Treatments were applied to turf foliage using DeVilbiss type sprayer. Pots were placed in growth chamber at 28° C., 95% humidity and 12 hours lighting at 400 uE/meter square.

The test pathogen Rhizoctonia solani was cultured on sterilized sorghum seed three weeks prior to test initiation. Two days after chemical treatment pots were inoculated by placing ten Rhizoctonia infested sorghum seed in each pot. Inoculated pots were returned to growth chamber and daylength was reduced to 8 hours to encourage Rhizoctonia infestation and brown patch symptoms.

Ten days after inoculation, test pots were removed from growth chamber and evaluated for disease and phytotoxicity. The percent Rhizoctonia brown patch infection was evaluated in each pot.

The test results are shown in Table IV.

TABLE IV

| EXAMPLE | CONCENTRATION OF TEST SOLUTION (mg/ml) | % CONTROL |
|---|---|---|
| 1 | 1 | 94 |
| | 0.2 | 87 |
| | 0.04 | 59 |
| 2 | 1 | 81 |
| | 0.2 | 49 |
| | 0.04 | 0 |
| 9 | 1 | 97 |
| | 0.2 | 94 |
| | 0.04 | 78 |
| 19 | 1 | 66 |
| | 0.2 | 50 |
| | 0.04 | 0 |

GREENHOUSE TEST FOR ACTIVITY ON PEANUT WHITE MOLD

The test pathogen Sclerotium rolfsii was cultured on sterilized oat seed for 21 days. The fungus/oat seed mixture was removed from culture flasks, air dried for 3 days, and then stored at room temperature until use (within 30 days). Following laboratory procedures set forth above peanut plants are each grown in 7.62 cm square pots for a period of 12-14 days. Then two ml solution of the test compound in acetone, water and Tween 20 are applied to the lower stem, foliage and soil surface of each pot. After twenty four hours, two grams of oat seed inoculum is placed over the soil surface of each pot. Pots are then incubated for 10 days in a growth chamber at 25°-28° C., 100% humidity with 12 hour light/12 hour dark photoperiod. The degree of disease for each plant was evaluated and rated as follows:
 1. No disease
 2. Slight disease—slight mycelium—no lesion
 3. Moderate disease—mycelium and small lesion
 4. Moderate/heavy disease—mycelium and lesion
 5. Heavy disease—plant collapse from disease

TABLE V

One rating for each treatment (four pots) is taken.

| Example | Amount of Test Compound (mg/pot) | Activity Rating |
|---|---|---|
| 1 | 1/.2/.04 | 1.0/1.0/2.0 |
| 2 | 1/.2/.04 | 1.0/2.5/4.0 |

TABLE V-continued

One rating for each treatment (four pots) is taken.

| Example | Amount of Test Compound (mg/pot) | Activity Rating |
|---|---|---|
| 3 | 1/.2/.04 | 1.0/3.5/4.0 |
| 4 | 1/.2/.04 | 1.0/2.25/3.25 |
| 8 | 1/.2/.04 | 2.0/2.25/4.0 |
| 11 | 1/.2/.04 | 1.25/1.0/1.5 |
| 12 | 1/.2/.04 | 2.75/4.5/4.75 |
| 28 | 1/.2/.04 | 1.0/1.75/4.25 |
| 34 | 1/.2/.04 | 1.0/1.0/2.75 |
| 38 | 1/.2/.04 | 1.5/1.0/2.25 |
| Example 10 of EPO Publication 0,276,177 | | 2.8/2.94/4.66* |

*Average of 2 or more test replications

As can be seen from the data above, the compounds of the present invention have good fungicidal activity. Certain of the compounds of the present invention have high fungicidal activity (Examples 1, 2, 8, 19 and 36) at low application rates for resulting cost savings and lower pesticide load on the environment. The compounds of the present invention generally exhibit good fungicide control with no or only mild transient plant injury. The compounds also exhibit safety to animals such as fish which may be contacted during use of the compounds.

The fungicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan).

Suitable dispersants are methyl, cellulose, polyvinyl alcohol, sodium lignin sulfonates, polymeric alkyl naphthalene sulfonates, sodium naphthalene sulfonate, polymethylene bisnaphthalene sulfonate and polyethyleneoxide-polypropyleneoxide copolymers.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

Suitable types of formulations are emulsifiable concentrates, flowables, wettable powders, dusts and granules. A suitable flowable formulaion (3lb/gal) (0.35 kg/1) is as follows:

| INGREDIENTS | % BY WGT |
| --- | --- |
| Compound of Example 9 | 31.14 |
| Xanthan gum | 1.25 |
| block copolymers of propylene oxide and ethylene oxide | 2.50 |
| magnesium aluminum silicate | 1.00 |
| lignosulfonate dispersant | 2.00 |
| defoamer | 0.25 |
| water | 61.86 |
| | 100.00 |

The compounds of the present invention generally appear to show the greatest activity when applied as a foliar spray.

The compositions of this invention can also contain other additaments, for example, other fungicides, fertilizers, insecticides, herbicides, other pesticides, safeners and the like used as adjuvants or in combination with any of the above described adjuvants. Fungicides useful in combination with the active ingredients of this invention included, for example, Tricyclazole
Pyroquilon
Chlorothalonil
Triadimenol
Fenpropimorph
Carbendazim
Triadimefon
Flusilazol
Metalaxyl Other suitable fungicides will be known to those skilled in the art.

When operating in accordance with the present invention, effective amounts of the compounds of this invention are applied to the foliage or vegetative propagules or may be incorporated into the soil or water around the foliage in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development of plants and disease, the type and condition of soil, the amount of rainfall and the specific compounds employed. In selective foliar application a dosage of from about 30 to about 500 g/ha preferably from about 60 to about 250 g/ha, is usually employed. In soil applications a dosage of from about 100 to about 1000 g/ha, preferably from about 250 to about 500 g/ha is usually employed. Lower or higher rates may be required in some instances. One skilled in the art can readily determine from this specification, including the above examples, the optimum rate to be applied in any particular case.

Although the invention is described with respect to specific modifications, the details thereof are not to be construed as limitations, for it will be apparent that various embodiments, changes and modifications may be resorted to without departing from the spirit and scope thereof and it is understood that such equivalent embodiments are intended to be included within the scope of this invention.

We claim:

1. A compound represented by the formula:

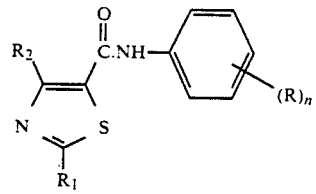

wherein each R is independently halo, halomethyl, 1-haloethyl, halomethoxy, 1-haloethoxy, halomethylthio, 1-haloethylthio, pentafluorosulfur, halomethylsulfinyl, 1-haloethylsulfinyl, halomethylsulfonyl or 1-haloethylsulfonyl; $R_1$ and $R_2$ are independently methyl, ethyl or fluoromethyl, provided that at least $R_1$ or $R_2$ is difluoromethyl or trifluoromethyl; and n is an integer from 3 to 5; or an agronomically acceptable salt thereof.

2. The compound of claim 1 wherein $R_1$ is methyl.

3. The compound of claim 2 wherein $R_2$ is trifluoromethyl.

4. The compound of claim 3 wherein each R is halo, halomethyl or halomethoxy.

5. The compound of claim 4 wherein each R is chloro, bromo, iodo, trihalomethyl or trihalomethoxy.

6. The compound of claim 4 wherein each R is chloro, bromo, trifluoromethyl or trifluoromethoxy.

7. The compound of claim 5 wherein n is from 3 to 4.

8. A compound represented by the formula:

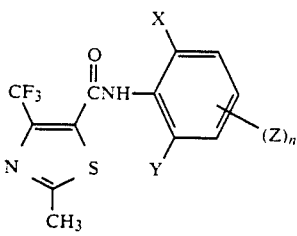

wherein X is halo, trihalomethyl or trihalomethoxy; Y is halo, trihalomethyl, trihalomethoxy, nitro or cyano; each Z is independently halo, trihalomethyl, trihalomethoxy, nitro or cyano; and n is an integer from 1 to 3; or an agronomically acceptable salt thereof.

9. The compound of claim 8 wherein X is halo, trifluoromethyl or trifluoromethoxy; Y is halo, trifluoromethyl, trifluoromethoxy, nitro or cyano; and each Z is independently halo, trifluoromethyl, trifluoromethoxy, nitro or cyano.

10. The compound of claim 9 wherein n is from 1 to 2.

11. A compound of the formula:

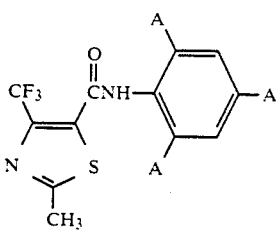

wherein each A is independently halo, trifluoromethyl or trifluoromethoxy, or an agronomically acceptable salt thereof.

12. A compound of the formula:

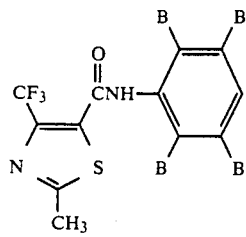

wherein each B is independently halo, trifluoromethyl or trifluoromethoxy, or an agronomically acceptable salt thereof.

13. A compound represented by the formula:

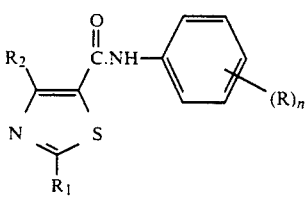

wherein each R is independently halo, halomethyl, 1-haloethyl, halomethoxy, 1-haloethoxy, pentafluorosulfur, halomethylsulfinyl, 1-haloethylsulfinyl, halomethylsulfonyl, 1-haloethylsulfonyl, nitro, cyano, halomethylthio, 1-haloethylthio, methylsulfinyl, ethylsulfinyl, methylsulfonyl, ethylsulfonyl, lower alkylcarbonyl or lower alkoxycarbonyl; $R_1$ is methyl or ethyl; $R_2$ is difluoromethyl or trifluoromethyl; and n is an integer from 3 to 5; or an agronomically acceptable salt thereof.

14. A composition comprising a fungicidally effective amount of a compound represented by the formula:

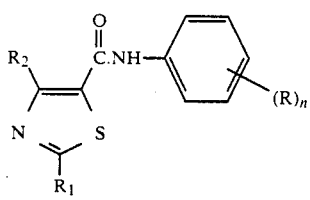

wherein each R is independently halo, halomethyl, 1-haloethyl, halomethoxy, 1-haloethoxy, halomethylthio, 1-haloethylthio, pentafluorosulfur, halomethylsulfinyl, 1-haloethylsulfinyl, halomethylsulfonyl or 1-haloethylsulfonyl; $R_1$ and $R_2$ are independently methyl, ethyl or fluoromethyl, provided at least $R_1$ or $R_2$ is difluoromethyl or trifluoromethyl; and n is an integer from 3 to 5; or an agronomically acceptable salt thereof.

15. The composition of claim 14 wherein $R_1$ is methyl.

16. The composition of claim 15 wherein $R_2$ is trifluoromethyl.

17. The composition of claim 16 wherein R is chloro, bromo, trifluoromethyl or trifluoromethoxy.

18. The composition of claim 17 wherein n is 3 or 4.

19. A method of controlling the growth of fungus disease on a plant comprising applying to the plant locus an effective amount of a compound represented by the formula:

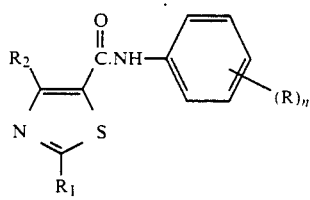

wherein each R is independently halo, halomethyl, 1-haloethyl, halomethoxy, 1-haloethoxy, halomethylthio, 1-haloethylthio, pentafluorosulfur, halomethylsulfinyl, 1-haloethylsulfinyl, halomethylsulfonyl or 1-haloethylsulfonyl; $R_1$ and $R_2$ are independently methyl, ethyl or fluoromethyl provided that at least $R_1$ or $R_2$ is difluoromethyl or trifluoromethyl; and n is an integer from 3 to 5; or an agronomically acceptable salt thereof.

20. The method of claim 19 wherein $R_1$ is methyl.

21. The method of claim 22 wherein $R_2$ is trifluoromethyl.

22. The method of claim 21 wherein R is chloro, bromo, trifluoromethyl or trifluoromethoxy.

23. The method of claim 22 wherein n is or 4.

24. The chemical compound of 2-methyl-4-trifluoromethyl-5-(2',6'-dibromo-4'-trifluoromethoxy carboxanilido) thiazole.

25. A composition comprising a fungicidally effective amount of the chemical compound of 2-methyl-4-trifluoromethyl-5(2',6'-dibromo-4'-trifuloromethoxy carboxanilido) thiazole.

26. A method of controlling the growth of fungus disease on a plant comprising applying to the plant locus an effective amount of the chemical compound of 2-methyl-4-trifluoromethyl-5-(2',6'-dibromo-4'-trifuloromethoxy carboxanilido) thiazole.

* * * * *

UNITED STATES PATENT AND TRADEMARK OFFICE
CERTIFICATE OF CORRECTION

PATENT NO. : 5,045,554

DATED : September 3, 1991

INVENTOR(S) : G. H. Alt et al.

It is certified that error appears in the above-identified patent and that said Letters Patent is hereby corrected as shown below:

| | | |
|---|---|---|
| Cover Page | | Under Attorney, Agent or Firm, remove "Sta4ley M. Tarter" and insert -- Stanley M. Tarter --. |
| Col. 2 | Line 62 | Remove "$CX_cH_{3-c}-CXH_{2-d}$" and insert -- "$CX_cH_{3-c}-CX_dH_{2-d}$ --. |
| Col. 3 | Line 5 | Remove "cyano, alkylthio," and insert -- cyano, lower alkylthio, --. |
| Col. 3 | Line 32 | Remove "preferably or 2." and insert -- preferably 1 or 2. --. |
| Col. 5 | Line 30 | Remove "2=methyl-4-trifluoromethyl-5-(2',6,-dibromo" and insert -- 2-methyl-4-trifluoromethyl-5-(2',6'-dibromo --. |
| Col. 6 | Line 34 | Remove "2-Methyl-4-dtrifuloromethyl" and insert -- 2-Methyl-4-trifluoromethyl --. |
| Col. 13 | Ex.#32 | Remove "N-(2,4,6-tribromphenyl)-" and insert -- N-(2,4,6-tribromophenyl)- --. |

UNITED STATES PATENT AND TRADEMARK OFFICE
CERTIFICATE OF CORRECTION

PATENT NO. : 5,045,554

DATED : September 3, 1991

INVENTOR(S) : G. H. ALT ET AL

It is certified that error appears in the above-identified patent and that said Letters Patent is hereby corrected as shown below:

Col. 26, line 36, Remove "Claim 22" and insert --Claim 20 -- line 40, Remove "wherein n is or 4." and insert -- wherein n is 3 or 4.--.

line 46, Remove "trifuloromethoxy" and insert --trifluoromethoxy--.

line 52, Remove "trifuloromethoxy" and insert --trifluoromethoxy--.

Signed and Sealed this

Sixteenth Day of February, 1993

Attest:

STEPHEN G. KUNIN

*Attesting Officer*   *Acting Commissioner of Patents and Trademarks*